United States Patent [19]

Cella et al.

[11] Patent Number: 4,864,034

[45] Date of Patent: Sep. 5, 1989

[54] SPIRO(BIS)INDANE BIS-OXYPHTHALIC ACIDS AND FUNCTIONAL DERIVATIVES THEREOF

[75] Inventors: James A. Cella, Clifton Park; Gary R. Faler, Scotia, both of N.Y.

[73] Assignee: General Electric Company, Schenectady, N.Y.

[21] Appl. No.: 146,155

[22] Filed: Jan. 20, 1988

[51] Int. Cl.$^4$ .................................................. C08G 63/62
[52] U.S. Cl. ..................................... 548/473; 549/241; 562/473; 562/466
[58] Field of Search .................. 548/473; 549/241; 562/473, 466

[56] References Cited

U.S. PATENT DOCUMENTS

| | | | |
|---|---|---|---|
| 3,725,070 | 4/1973 | Hamb et al. | 430/533 |
| 3,879,428 | 4/1975 | Heath | 549/421 |
| 4,116,980 | 9/1978 | Webb | 549/421 |
| 4,128,574 | 12/1978 | Markezich | 562/473 |
| 4,247,464 | 1/1981 | Relles | 548/461 |
| 4,257,953 | 3/1981 | Williams | 548/461 |
| 4,273,712 | 6/1981 | Williams | 548/461 |
| 4,329,292 | 5/1982 | Webb | 549/241 |
| 4,329,496 | 5/1982 | Webb | 562/548 |
| 4,736,016 | 4/1988 | Brunelle et al. | 528/370 |

Primary Examiner—Mukund J. Shah
Assistant Examiner—C. L. Cseh
Attorney, Agent, or Firm—William H. Pittman; James C. Davis, Jr.

[57] ABSTRACT

Spiro(bis)indane bis-oxyphthalic acid bisimides are prepared by the reaction of a nitro- or halo-substituted phthalimide with a salt of a 6,6'-dihydroxy-3,3,3'3'-tetramethylspiro(bis)indane. The bisimides may be converted to the corresponding dianhydrides, which react with diamines to form polyetherimides, or to the free tetracarboxylic acids or their salts, esters or amides.

8 Claims, No Drawings

SPIRO(BIS)INDANE BIS-OXYPHTHALIC ACIDS AND FUNCTIONAL DERIVATIVES THEREOF

This invention relates to new compositions of matter, and more particularly to intermediates for the preparation of polyimides containing spiro(bis)indane moieties.

Polyimides are typically prepared by the reaction of tetracarboxylic acid dianhydrides with diamines. Many types of polyimides are known, including polyetherimides which have highly desirable properties as engineering thermoplastics. Examples of polyetherimides of this type are those derived from 2,2-bis[4-(3,4-dicarboxyphenoxy)-phenyl]propanedianhydride. Other functional derivatives of the same tetracarboxylic acid, including bisimides such as the bis(N-methylimide) (hereinafter "BPABI"), are known.

In copending, commonly owned application Ser. No. 40,528, filed Apr. 20, 1987, there are disclosed polycarbonates derived from spiro(bis)indanes, particularly 6,6'-dihydroxy-3,3,3',3'-tetramethylspiro(bis)indane (hereinafter "SBI"). These polycarbonates have beneficial properties in comparison to such other known polycarbonates as bisphenol A polycarbonates, including very low birefringences. It is of interest to prepare other polymers containing spiro(bis)indane moieties, which are related in the same way to the corresponding bisphenol A-derived polymers. The present invention is directed to an essential intermediate in the preparation of many of such polymers, particularly polyetherimides.

Accordingly, the present invention includes spiro(bis)indane bis-oxyphthalic compounds of the formula

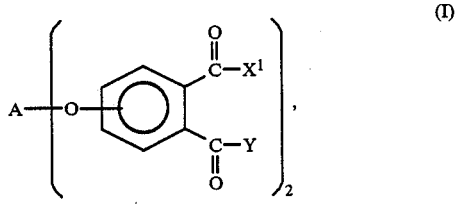

(I)

wherein A is a spiro(bis)indane moiety of the formula

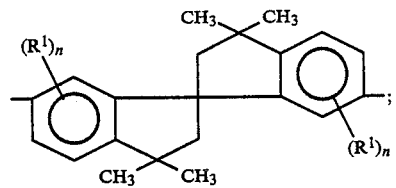

(II)

$X^1$ and Y are each OH, OM, $OR_2$

or or $X^1$ and Y taken together are O or $NR^2$; each $R^1$ is independently $C_{1-4}$ primary or secondary alkyl or halo; each of $R^2$ and $R^3$ is a $C_{1-8}$ alkyl or $C_{6-20}$ aryl radical; M is one equivalent of a cation and n is 0-3.

The spiro(bis)indane units of formula II are obviously derived from 6,6'-dihydroxy-3,3,3',3'-tetramethylspiro(bis)indanes (hereinafter sometimes simply "spirobiindanes"), which may be substituted or unsubstituted. The $R^1$ values therein may be alkyl radicals such as methyl, ethyl, 1-propyl or 2-propyl, or halo atoms such as chloro or bromo. Among compounds containing such $R^1$ values, methyl and chloro are preferred; however, the most preferred compounds of this invention are those derived from SBI, in which n is 0.

It will be apparent from formula I that the compounds of this invention include bis-oxyphthalic acids and their slats, esters, amides, anhydrides and imides. The preferred compounds are the bis(3,4-dicarboxy) compounds and especially the dianhydrides and bisimides; among bisimides, the preferred ones are those in which $R^2$ is $C_{1-4}$ primary or secondary alkyl and especially methyl.

The bisimides of this invention may be prepared by the reaction of SBI salts with nitro- or halo-substituted phthalimides. The methods for such preparation are identical to those used in preparing BPABI. Said bisimides may be converted to dianhydrides, also by known methods. For suitable methods for bisimide and dianhydride preparation, reference is made to the following U.S. patents, the disclosures of which are incorporated by reference herein:

3,879,428
4,257,953
4,116,980
4,273,712
4,128,574
4,329,292
4,247,464
4,329,496

Also capable of preparation by conventional methods from the bisimides and dianhydrides are the free tetracarboxylic acids and their salts, esters and amides.

The preparation of the bisimides and dianhydrides of this invention is illustrated by the following examples.

EXAMPLE 1

SBI, 15.4 grams (50 mmol.), was added portionwise to a slurry of 262 grams (102 mmol.) of sodium hydride in 100 ml. of dry dimethylformamide. The mixture was heated for one hour at 75° C. in a nitrogen atmosphere, after which 20.6 grams (100 mmol.) of 4-nitro-N-methylphthalimide was added. The resulting mixture was heated for 1½ hours at 110° C., cooled and poured into 3 volumes of cold water. The solid which precipitated was filtered and suspended in a mixture of toluene and 2% aqueous sodium hydroxide solution and the mixture was cooled and filtered; the organic phase of the filtrate was dried and vacuum stripped. The combined solids were the desired 6,6'-bis(3,4-dicarboxyphenoxy)-3,3,3',3'-tetramethylspiro(bis)indane bis-N-methylimide (27.07 grams, 86.5% of theoretical). Its melting point after recrystallization from toluene was 217.5°-218° C. The structure was confirmed by proton nuclear magnetic resonance and field desorption mass spectrometry.

EXAMPLE 2

A solution of 14 grams (22.36 mmol.) of the bisimide of Example 1 in 16.7 grams of a 45% aqueous potassium hydroxide solution and 20 ml. of water was heated under reflux, with water and methylamine being removed by distillation and water being replenished. Heating was continued for 4 days, until the distillate was neutral to pH paper. The solution was cooled and added slowly to cold concentrated hydrochloric acid, and the tetracarboxylic acid which precipitated was collected by filtration, dried and dissolved in a mixture of 25 ml. of chlorobenzene and 5 ml. of acetic anhydride. Upon heating under reflux for 2½ hours and cooling, the desired dianhydride (10.3 grams, 77% of theoretical) precipitated and was filtered and dried; it melted at 233°–234° C. The structure was confirmed spectroscopically as for the bisimide.

The dianhydrides of this invention (and, by extension, other derivatives of the tetracarboxylic acids by way of their conversion to dianhydrides) may be converted to polyetherimides by reaction with diamines. The methods for such conversion are well known in the art and need not be disclosed in detail herein.

The dianhydrides are also capable of conversion to cyclic polyetherimides and cyclic polyamideimides. Such cyclic materials are disclosed and claimed in copending, commonly owned application Ser. No. 146,154 filed Jan. 20, 1988. For this purpose, approximately equimolar proportions of diamine and dianhydride may be heated at a temperature in the range of about 120°–250° C., with water of reaction being removed by distillation. It is frequently preferred to employ a relatively high boiling organic solvent, typically a chlorinated aromatic hydrocarbon such as o-dichlorobenzene or a dipolar aprotic solvent such as dimethyl sulfoxide or dimethylacetamide. The presence of a metal carboxylate or oxygenated phosphorus compound as a catalyst, in accordance with U.S. Pat. Nos. 4,293,683 and 4,324,882, is also often beneficial. The disclosures of these patents are also incorporated by reference herein.

Macrocyclic polyamideimide oligomers, as well as polyamideimides, may be converted to copolyamideimides by reaction with at least one lactam of the formula

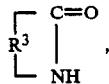

wherein $R^3$ is a divalent aliphatic hydrocarbon or substituted hydrocarbon radical containing a chain of about 2-20 carbon atoms, in the presence of a basic reagent.

Any of a number of known lactams may be used. Preferred are those in which $R^3$ is a straight alkylene chain containing about 4-12 carbon atoms. Illustrative lactams are pivalolactam, δ-valerolactam, ε-caprolactam and laurolactam, in which $R^3$ is $CH_2C(CH_3)_2$, $(CH_2)_4$, $(CH_2)_5$ and $(CH_2)_{11}$, respectively. ε-Caprolactam is especially preferred.

The basic reagents include inorganic bases such as the alkali and alkaline earth metals and their hydrides, hydroxides, carbonates and alkoxides, and strong organic bases such as tetraalkylammonium hydroxides, guanidines, and organometallics including Grignard reagents and organolithium reagents. The alkali metal hydrides, especially sodium hydride, are preferred.

The reaction between the lactam, basic reagent and macrocyclic polyamide oligomer composition typically takes place at elevated temperatures. In general, temperatures of about 25°–200° C., preferably about 90°–150° C., are adequate to effect reaction of the lactam with the basic reagent to form an anionic intermediate, which subsequently reacts with the oligomer composition at temperatures in the range of about 200°–300° C. The proportions of lactam and oligomer composition are not critical but may be varied according to the desired stoichiometry of the product.

Macrocyclic copolyimides in which a portion of the acid-derived moieties contain sulfur may be prepared by employing a dianhydride mixture including a compound such as bis(3,4-dicarboxyphenyl) sulfide dianhydride. They may be converted to linear polyimides by reaction with at least one basic sulfide of the formula $M-S-X^2$, wherein M is an alkali metal (usually sodium) and $X^2$ is M or an aryl radical, preferably phenyl. The basic sulfide is generally employed in the amount of about 2-10 mole percent, preferably about 3-6 mole percent, based on structural units in the cyclic imide composition. The polymerization reaction may be conducted in bulk or in solution, typically in a polar aprotic solvent such as dimethylformamide, dimethylacetamide or dimethyl sulfoxide, and is generally conducted at temperatures in the range of about 150°–225° C. The polymerization mechanism involves ring-opening of the cyclic imide at the sulfur atom.

Macrocyclic polyimides containing a disiloxane group as part of one of the acids or amines can be polymerized by the action of a strongly acidic catalyst such as methanesulfonic or trifluoromethanesulfonic acid, a basic catalyst such as an alkali metal phenate, or an alkali metal fluoride. Among the latter, cesium fluoride is frequently preferred because of its high solubility in the macrocyclic disiloxane polyimides. It is also possible to incorporate in the polymerization mixture a cyclic polysiloxane such as cyclooctamethyltetrasiloxane, to increase the molecular weight of the polysiloxane blocks in the linear polyimide product.

The proportion of catalyst in the mixture, based on macrocyclic polyimide and cyclic polysiloxane present, may vary widely and is typically about 0.001-10.0 mole percent. Polymerization temperatures are typically in the range of about 125°–200° C. It may sometimes be advantageous to employ a non-polar solvent such as o-dichlorobenzene or 1,2,4-trichlorobenzene as a reaction medium.

The preparation of macrocyclic polyetherimides and polyamideimides, and their conversion to linear polymers, are illustrated by the following examples.

EXAMPLE 3

To a solution of 1.081 grams (10 mmol.) of m-phenylenediamine and 18 mg. of sodium phenylphosphonate in 120 ml. of o-dichlorobenzene was added slowly at 130° C., with stirring, a solution of 6 grams (10 mmol.) of the dianhydride of Example 2 in 60 ml. of hot o-dichlorobenzene. Heating at 130° C. was continued for 1½ hours, after which the temperature was raised to 225° C. and water and solvent were removed by distillation to a total of 90 ml. The solution was heated under reflux for 3 hours, cooled and poured into 600 ml. of methanol. The solids which precipitated were extracted in a Soxhlet extractor with acetone for 18 hours. The residue from the extraction was a linear polyimide having a weight average molecular weight greater than 100,000. Upon evaporation of the acetone from the extracts, there was obtained a white powder which was shown by field desorption mass spectrometry to comprise principally the macrocyclic polyetherimide dimer. The yield was about 75% of theoretical.

EXAMPLE 4–7

The procedure of Example 3 was repeated, substituting the following diamines for the m-phenylenediamine on an equimolar basis:
Example 4—p-phenylenediamine;

Example 5—bis(4-aminophenyl)methane;
Example 6—4-aminophenyl ether;
Example 7—9,9,bis(4-aminophenyl)fluorene.

The product of Example 4 ws insoluble in methanol and comprised a mixtured of linear polyetherimide and macrocyclic oligomers.

EXAMPLE 8

To a solution of 1.03 grams (4.54 mmol.) of 3,3'-diaminobenzanilide and 15 mg. of sodium pyrophosphate in 280 ml. of o-dichlorobenzene was added under reflux over ½ hour, with stirring, a solution of 2.72 grams (4,54 mmol.) of the dianhydride of Example 2 in 30 ml. of warm o-dichlorobenzene. Refluxing was continued for 2 hours, after which the water and solvent were removed by distillation to a total of 180 ml. The solution was cooled and poured into 500 ml. of rapidly stirred methanol. The solids which precipitated were extracted in a Soxhlet extractor with acetone. The residue from the extraction was a linear polyamideimide. Upon evaporation of the acetone from the extracts, there was obtained a white powder which was shown by field desorption mass spectrometry to comprise principally the macrocyclic polyamideimide dimer. The yield was about 7-% of theoretical.

EXAMPLE 9

A solution of 1.274 grams (5 mmol.) of 1.9-diamino-4,4,6,6-tetramethyl-4,6-disila-5-oxanonane in 50 ml. of 0-dichlorobenzene was added over 1 hour to a solution of 3 grams (5 mmol.) of the dianhydride of Example 2 and 2 mg. of sodium phenylphosphonate in 250 ml. of o-dichlorobenzene, at 140° C. When the addition was completed, the temperature was raised to 225° C. and o-dichlorobenzene and water were removed by distillation until the distillate was no longer cloudy; a total of about 100 ml. of o-dichlorobenzene was thus removed. The residual solution was heated under reflux for 2 hours and then reduced to about 10% of its original volume by distillation. Upon cooling and pouring into 5 volumes of methanol, a solid precipitated which was collected by filtration and dried in a vacuum oven at 110° C. It was shown by field desorption mass spectrometry to comprise the desired macrocyclic siloxane polyetherimide monomer and dimer. A further portion of macrocyclic monomer was obtained by evaporation of the methanol from the filtrate. The total yield of macrocyclic oligomers was 3.34 grams, or 82% of theoretical.

EXAMPLE 10

The procedure of Example 9 was repeated, replacing the diamine on an equimolar basis with bis(3-aminophenyl)tetramethyldisiloxane. There was obtained 3.87 grams (85% of theoretical) of a white solid comprising a mixture of linear siloxane polyetherimide and macrocyclic oligomers.

EXAMPLE 11

A mixture of 1 gram of the crude macrocyclic polyamideimide oligomer mixture of Example 8, 10 grams of caprolactam and 290 mg. of sodium hydride was heated in a test tube at 150° C. in a nitrogen atmosphere for ½ hour, during which time melting occurred and hydrogen was evolved. It was then heated for 12 minutes at 230° C. and cooled. The solid product was extracted with tetrahydrofuran, leaving as the insoluble product a linear copolyamideimide having a weight average molecular weight of 27,000.

EXAMPLE 12

A solution of 26.7 mg. of the macrocyclic siloxane polyetherimide monomer product of Example 9 and 1 microliter of methanesulfonic acid in 100 ml. of 1,2,4-trichlorobenzene was heated at 140° C. for one hour, with periodic analysis by gel permeation chromatography. After 40 minutes the weight average molecular weight relative to polystyrene was about 20,000 and no further increase was noted.

The solution was poured onto a glass plate and allowed to thicken overnight. It was then heated in a vacuum oven for 2 hours at 140° C., yielding a clear, colorless film with excellent integrity. The film had a weight average molecular weight of about 200,000 and a glass transition temperature of 109° C.

EXAMPLE 13

A mixture of 25 mg. of the macrocyclic siloxane polyetherimide monomer product of Example 9 and 1 microliter of methanesulfonic acid was heated for 10 minutes at 250° C., after which gel permeation chromatographic analysis showed a weight average molecular weight relative to polystyrene of 26,200. The product was cooled, dissolved in chloroform and cast on a glass slide which was then heated for 1 hour at 140° C., to produce a polymer film with a molecular weight of 39,800.

What is claimed is:

1. A spiro(bis)indane bis-oxyphthalic compound of the formula

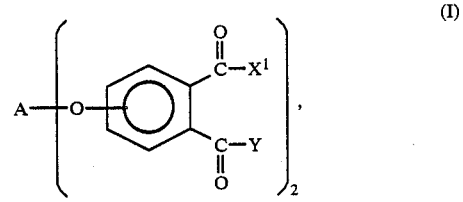

wherein A is a spiro(bis)indane moiety of the formula

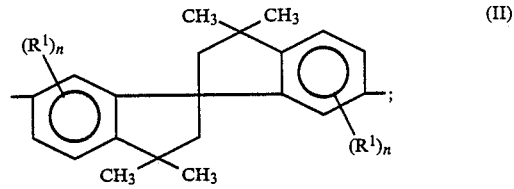

$X^1$ and Y are each OH, OM, $OR^2$

or or $X^1$ and Y taken together are O or $NR^2$; each $R^1$ is independently $C_{1-4}$ primary or secondary alkyl or halo; each of $R^2$ and $R^3$ is a $C_{1-8}$ alkyl or $C_{6-20}$ aryl radical; M is one equivalent of a cation and n is 0.3.

2. A compound according to claim 1 wherein $X^1$ and Y taken together are O or $NR^2$.

3. A compound according to claim 2 wherein n is O.

4. A compound according to claim 2 which is a bis(3,4-dicarboxy) compound.

5. A compound according to claim 4 wherein $X^1$ and Y taken together are O.

6. A compound according to claim 4 wherein $X^1$ and Y taken together are $NR^2$.

7. A compound according to claim 6 wherein $R^2$ is $C_{1-4}$ primary or secondary alkyl.

8. A compound according to claim 7 wherein $R^2$ is methyl.

* * * * *